US010434238B2

(12) United States Patent
Pesenti et al.

(10) Patent No.: US 10,434,238 B2
(45) Date of Patent: Oct. 8, 2019

(54) EXTRACORPOREAL CIRCUIT FOR $CO_2$ REMOVAL FROM BLOOD

(71) Applicant: Xenios AG, Heilbronn (DE)

(72) Inventors: Antonio Pesenti, Milan (IT); Alberto Zanella, Milan (IT); Domenico Salerno, Milan (IT); Nicolò Antonino Patroniti, Milan (IT); Francesco Mantegazza, Milan (IT)

(73) Assignee: Xenios AG, Heilbronn (DE)

( * ) Notice: Subject to any disclaimer, the term of this patent is extended or adjusted under 35 U.S.C. 154(b) by 423 days.

(21) Appl. No.: 15/500,835

(22) PCT Filed: Jul. 31, 2015

(86) PCT No.: PCT/IB2015/055837
§ 371 (c)(1),
(2) Date: Jan. 31, 2017

(87) PCT Pub. No.: WO2016/016870
PCT Pub. Date: Feb. 4, 2016

(65) Prior Publication Data
US 2017/0224898 A1    Aug. 10, 2017

(30) Foreign Application Priority Data
Aug. 1, 2014  (IT) .............................. TO2014A0623

(51) Int. Cl.
*A61M 1/34*      (2006.01)
*A61M 1/16*      (2006.01)
(Continued)

(52) U.S. Cl.
CPC ........ *A61M 1/3482* (2014.02); *A61M 1/1698* (2013.01); *A61M 1/32* (2013.01);
(Continued)

(58) Field of Classification Search
CPC .............. A61M 1/3482; A61M 1/3479; A61M 1/1698; A61M 1/32; B01D 61/145; B01D 61/42; B01D 61/58
See application file for complete search history.

(56) References Cited

U.S. PATENT DOCUMENTS

| 3,579,441 A | 5/1971 | Brown |
| 2011/0168614 A1 | 7/2011 | Pouchoulin et al. |

(Continued)

FOREIGN PATENT DOCUMENTS

| DE | 102012020497 A1 | 4/2014 |
| IT | BO20090437 A1 | 1/2011 |

(Continued)

OTHER PUBLICATIONS

Machine Translation of Hemodec (IT BO20090437), using Google Translate (Year: 2019).*

(Continued)

*Primary Examiner* — Ariana Zimbouski
(74) *Attorney, Agent, or Firm* — Dinsmore & Shohl LLP

(57) ABSTRACT

The present invention relates to an extracorporeal circuit for $CO_2$ removal from blood comprising a line for taking blood from the patient, a decarboxylation assembly and a line for returning the blood to the patient; said decarboxylation assembly comprising a first filtering unit, an oxygenator, an electrodialyzer adapted to generate an acid solution and a basic solution and means for the infusion of said acid solution upstream of said oxygenator, wherein said electrodialyzer comprises a first electrodialysis chamber and a second electrodialysis chamber, said first and second electrodialysis chambers being separated by an ionic membrane, and wherein said first chamber and said second chamber are (Continued)

respectively separated from the positive electrode, or anode, and from the negative electrode, or cathode, by means of a bipolar membrane.

12 Claims, 6 Drawing Sheets

(51) Int. Cl.
*A61M 1/32* (2006.01)
*B01D 61/14* (2006.01)
*B01D 61/42* (2006.01)
*B01D 61/58* (2006.01)

(52) U.S. Cl.
CPC ......... *A61M 1/3479* (2014.02); *B01D 61/145* (2013.01); *B01D 61/42* (2013.01); *B01D 61/58* (2013.01); *A61M 2202/0225* (2013.01)

(56) References Cited

U.S. PATENT DOCUMENTS

| | | |
|---|---|---|
| 2011/0237996 A1 | 9/2011 | Kotanko et al. |
| 2011/0264025 A1 | 10/2011 | Lannoy |
| 2014/0158588 A1 | 6/2014 | Pudil et al. |
| 2014/0217028 A1 | 8/2014 | Pudil et al. |

FOREIGN PATENT DOCUMENTS

| | | |
|---|---|---|
| WO | WO-2008/135282 A2 | 11/2008 |
| WO | 2011130528 A1 | 10/2011 |
| WO | 2016016870 A1 | 2/2016 |

OTHER PUBLICATIONS

International Search Report and Written Opinion of Application No. PCT/IB2015/055837 dated Nov. 23, 2015.

* cited by examiner

EXTRACORPOREAL CIRCUIT FOR $CO_2$ REMOVAL FROM BLOOD

RELATED APPLICATIONS

This application is a 35 U.S.C. § 371 National Stage filing of International Application No. PCT/IB2015/055837 filed on Jul. 31, 2015, which claims the benefit of Italian Patent Application No. TO2014A000623 filed on Aug. 1, 2014. The entire contents of each of the foregoing applications are explicitly incorporated herein by reference.

TECHNICAL FIELD

The present invention relates to an extracorporeal circuit for $CO_2$ removal from blood.

Extracorporeal $CO_2$ removal from blood is necessary when pulmonary function must be compensated for, even though partially, as it is seriously compromised due to different diseases.

BACKGROUND ART

In general, extracorporeal circuits for $CO_2$ removal from blood allow the patient's blood to be drained in an extracorporeal circuit in order to be artificially oxygenated and decarboxylated by means of a gas exchanger, such as an oxygenator. In particular, in a veno-venous extracorporeal system, venous blood returning towards the right atrium of the heart is collected in the extracorporeal circuit, pumped into the oxygenator and from there it is then reintroduced into the venous system.

The most commonly used oxygenators are membrane oxygenators, in which blood and oxygen (or a mixture rich in oxygen) are caused o flow on opposite sides of a membrane. Therefore, these types of apparatuses act upon the quantity of $CO_2$ dissolved in the blood, which actually turns out to be a limited portion of the total content of $CO_2$. As a matter of fact, it is known that 90% of the $CO_2$ transported in blood is available in the form of bicarbonate ions according to the chemical equilibrium (I) below.

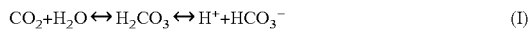

$$CO_2 + H_2O \leftrightarrow H_2CO_3 \leftrightarrow H^+ + HCO_3^- \quad (I)$$

A solution to increase $CO_2$ removal from blood by means of membrane oxygenators can be the one of acting upon the chemical equilibrium (I) by causing an increase in the percentage of gaseous $CO_2$. In this way, by increasing the concentration of gaseous $CO_2$ as the target of the removal operated by the oxygenator, total $CO_2$ removal from blood is improved.

One of the ways to act upon the chemical equilibrium (I) in favour of gaseous $CO_2$ is exogenous acidification. The aforesaid exogenous acidification is carried out by adding an acid substance to the extracorporeal circuit upstream of the oxygenator.

Said acidification, by turning bicarbonate ions into dissolved $CO_2$, increases the transmembrane $pCO_2$ gradient, thus increasing the transfer of $CO_2$ through the membrane of the oxygenator. Exogenous acidification of blood ensures the removal of the equivalent of 50% of the total production of $CO_2$ of an adult man from an extracorporeal blood equalling 250 ml/min.

As an alternative, a technique based on ventilation of acidified dialysate was developed, which proved to be slightly less efficient (10-15%) than direct ventilation of blood, but reduces the exogenous surface in contact with the blood and, therefore, can have possible advantages.

In both cases, the acidification is obtained through infusion of a concentrated solution of metabolizable organic acid, for example lactic acid. However, when they are infused in an exogenous manner, despite their high clearance, they can cause a certain level of metabolic acidosis and a slight increase in the total corporeal production of $CO_2$.

Therefore, as a person skilled in the art can easily understand, this addition of acid can reduce the efficiency of the extracorporeal $CO_2$ removal technique and can lead to a series of drawbacks, which must be handled without altering the patient's homeostasis.

ITBO20090437 describes an extracorporeal circulation system, in which the removal of $CO_2$ and bicarbonates is operated by means of a device for the electrolysis of plasmatic water. However, this device uses pure water and, as a drawback, it does not allow current to properly circulate and, therefore, it cannot ensure an effective ion separation. Furthermore, the fact that one of electrodes is arranged in direct contact with plasmatic water causes the formation of gaseous chlorine, which is notoriously toxic, and the precipitation of calcium carbonates, which can cause pulmonary embolisms.

DISCLOSURE OF INVENTION

Therefore, the object of the present invention is to provide an extracorporeal circuit for $CO_2$ removal from blood, which is able to remove increased $CO_2$ by acting upon the chemical equilibrium (I), without the help of the addition of an exogenous acid, though ensuring, at the same time, high safety levels.

According to the present invention there is provided an extracorporeal circuit for $CO_2$ removal from blood, whose essential features are set forth in claim 1 and whose preferred and/or auxiliary features are set forth in claims 2 to 12.

In particular, there is provided an extracorporeal circuit for $CO_2$ removal from blood comprising a decarboxylation assembly comprising a first filtering unit, an oxygenator, an electrodialyzer adapted to generate an acid solution and a basic solution and means for the infusion of the acid solution upstream of the oxygenator.

Advantageously, the use of an electrodialysis technique on an electrolyte solution, for example a dialysate or an ultrafiltrate, allows the electrolytes present in the solution to be moved in a controlled manner, thus generating an acid solution without the addition of exogenous substances.

In particular, thanks to an electrodialysis unit, one can obtain a regional acidification, so as to improve the extracorporeal removal of carbon dioxide acting upon the chemical equilibrium (I) mentioned above.

In an embodiment, the first filtering unit is a filter selected in the group consisting of a haemodiafilter, a haemofilter and a dialyzer.

The circuit according to the present invention can further comprise a second filtering unit arranged upstream of the electrodialyzer. In particular, the second filtering unit can be a filter for calcium.

In an embodiment of the invention, the circuit comprises, furthermore, infusion means for the infusion of the basic solution downstream of the first filtering unit.

BRIEF DESCRIPTION OF THE DRAWINGS

The present invention will be best understood upon perusal of the following detailed description used by way of a mere non-limiting example, with reference to the accompanying drawings, wherein.

BEST MODE FOR CARRYING OUT THE INVENTION

Figure 1:
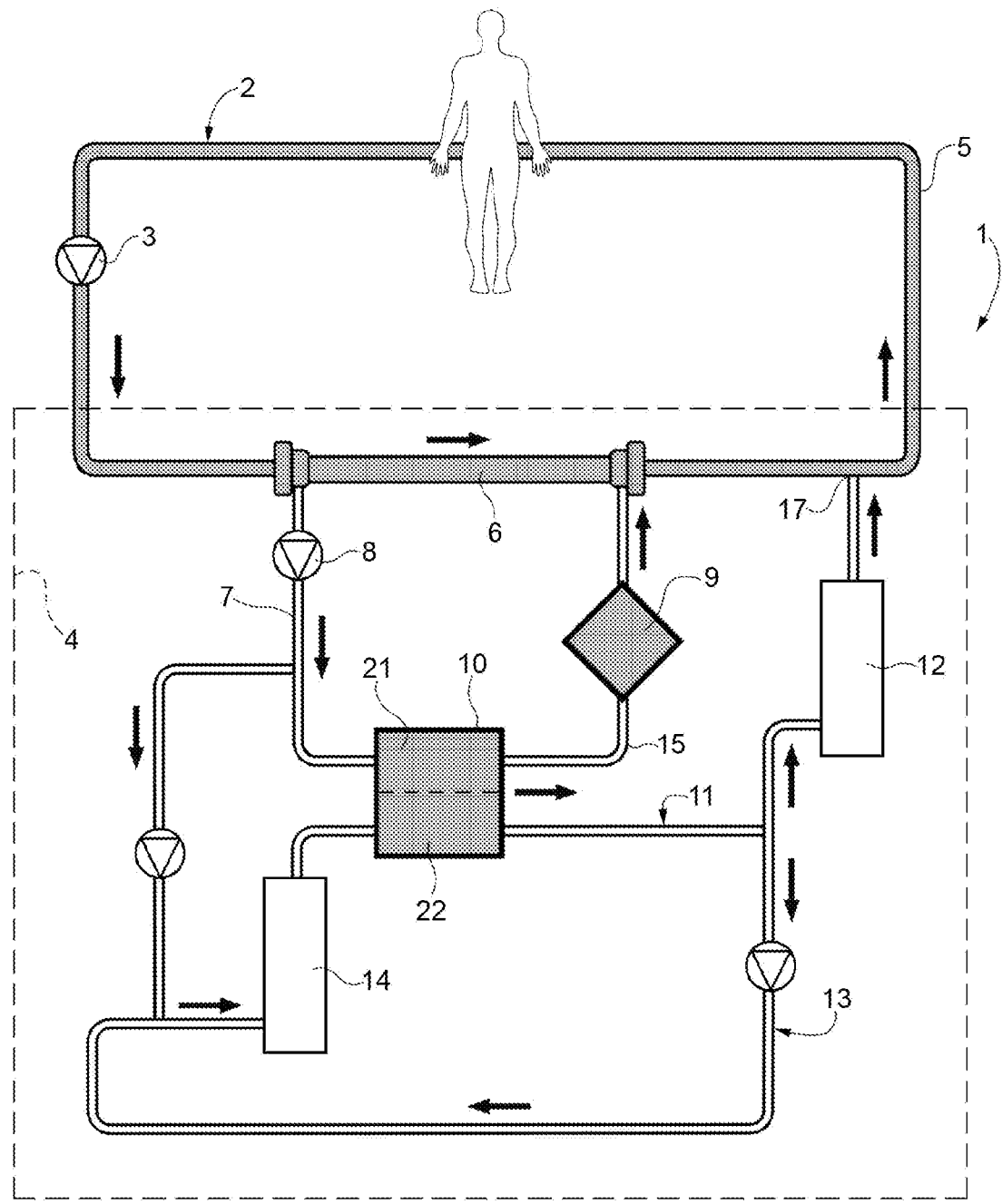
FIG. 1 shows a first embodiment of the invention.

In FIG. 1 number 1 indicates, as a whole, an extracorporeal blood removal circuit according to a first embodiment of the present invention.

The circuit 1 comprises a line for taking blood 2 from the patient, upon which a peristaltic pump 3 acts, a decarboxylation assembly 4 and a line for returning the blood 5 to the patient.

The decarboxylation assembly 4 comprises a haemodiafilter 6, acting as the first filtering unit, which is connected to an ultrafiltrate circuit 7, upon which a peristaltic pump 8 acts, an oxygenator 9 arranged on the circuit 7, and an electrodialyzer 10, which is adapted to generate an acid solution, which is carried upstream of the oxygenator following the recirculation flow along the line 15.

Figure 2:
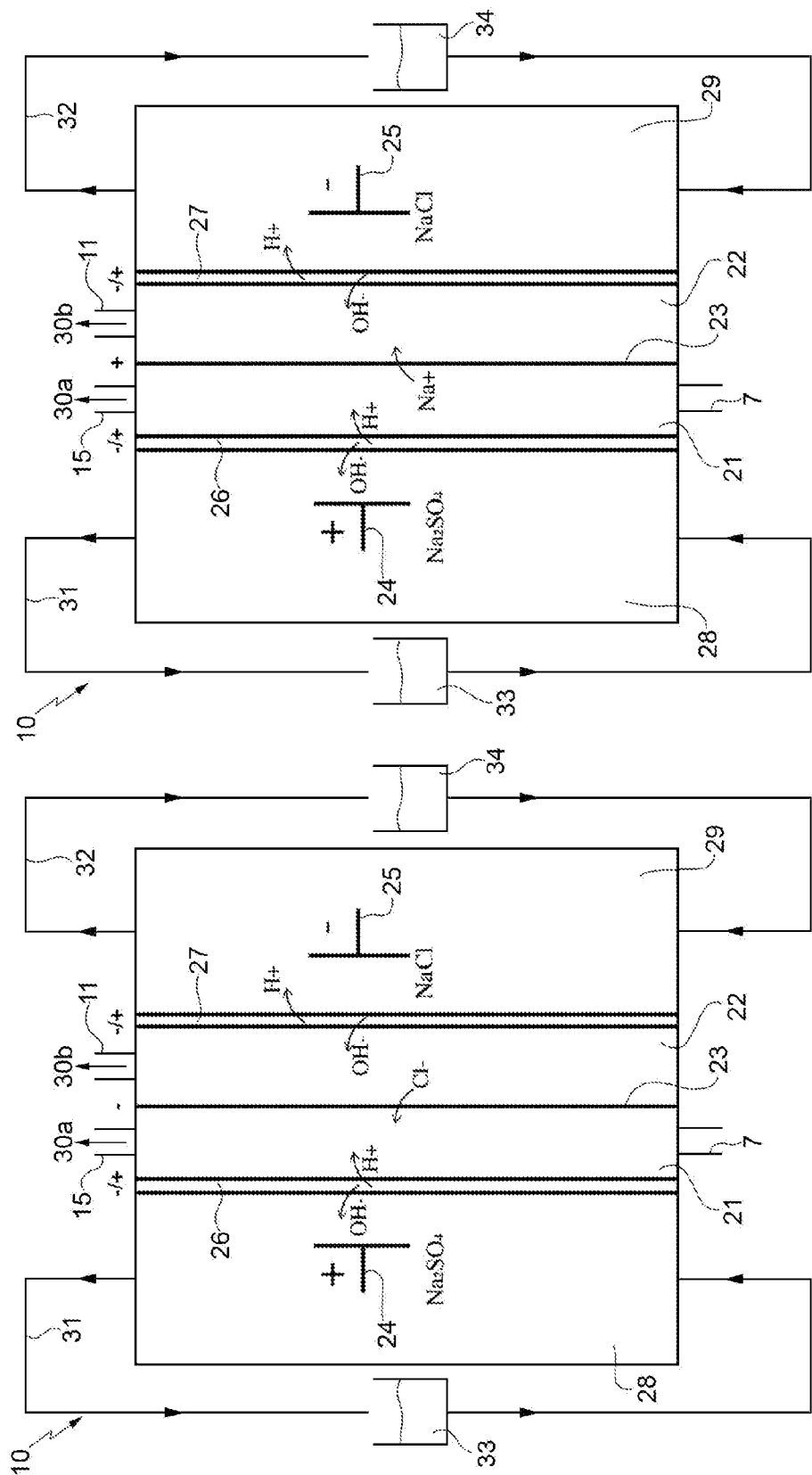
FIG. 2 shows a detail of the electrodialyzer of FIG. 1.

As shown in FIG. 2a, in an embodiment of the invention, the electrodialyzer 10 is provided with a first electrodialysis chamber 21 and a second electrodialysis chamber 22, which are separated by an ionic membrane 23. Each chamber is separated from the corresponding electrode 24, 25 by means of a bipolar membrane 26, 27. The positive electrode 24, or anode, is arranged in a chamber 28 immersed is an anolyte solution, for example sodium sulfate or sodium phosphate, and the negative electrode 25, or cathode, is arranged in a chamber 29 immersed in a catholyte solution, for example sodium chloride. The anolyte and catholyte solutions are isotonic with plasmatic water.

According to FIG. 2a, the ionic membrane 23 is an anionic membrane, the electrodialysis chamber 21 associated with the anode 24 is adapted to generate an acid solution and the electrodialysis chamber 22 associated with the cathode 25, on the other hand, is adapted to generate a basic solution.

Advantageously, the presence of the bipolar membranes 26 and 27 prevents the ions contained in the chambers 21 and 22 from moving towards the chambers 28 and 29 and vice versa.

In this way, the acid solution and the basic solution are not contaminated with ions coming from the catholyte solution or the anolyte solution.

Furthermore, the ions contained in the acid solution and in the basic solution are prevented from moving towards the anode 24 and the cathode 25, thus avoiding the formation of highly toxic substances, such as gaseous chlorine, as well as the gathering of substances on the electrodes, which might reduce their efficiency.

The anolyte solution and the catholyte solution are respectively recirculated inside the chambers 28 and 29 by means of the circuits 31 and 32 through the pumps 33 and 34. On said circuits 31 and 32 there are provided degassers 33 and 34, which eliminate the gases developed during the electrodialysis, typically gaseous oxygen and hydrogen.

The blood, taken from the patient through the line 2, is pushed by the peristaltic pump 3 towards the haemodiafilter 6. The haemodiafilter 6 separates the ultrafiltrate or plasmatic water. Part of the plasmatic water pushed by the pump 8 reaches the electrodialyzer 10, where, in proportion to the electrical current applied, the plasmatic water entering the second chamber 22, which is "basic", provides anions to the plasmatic water present in the first chamber 21, which is "acid". Since the main anion in plasmatic water is $Cl^-$, the plasmatic water flowing in the first chamber 21 becomes rich in $Cl^-0$ ions, whereas $H^+$ ions are provided through the bipolar membrane 26.

Therefore, in the chamber 21 a flow of acid solution flow is formed, namely the acid plasmatic water 30a, whereas in the chamber 22 a flow of basic plasmatic water 30b is formed. The acid plasmatic water 30a and the basic plasmatic water 30b are isotonic with the plasmatic water of the circuit 7 flowing out of the first filtering unit 6.

Alternatively, the ionic membrane 23 can be a cationic membrane, as shown in FIG. 2b. In this case, the flow of ions on the inside of the electrodialyzer 10 is the one shown in the figure. Other configurations of the electrodialyzer 10 shown, for example with a plurality of acid chambers and basic chambers, are equally suited to solve the technical problem of the present invention.

As shown in FIG. 1, the outlet of the chamber 21 is arranged on the circuit 7. Therefore, the acid plasmatic water 30a flowing out of the electrodialyzer 10 is led through the line 15 to the oxygenator, for example a bubble oxygenator.

Advantageously, the acidification of the plasmatic water causes a shift in the chemical equilibrium (I) in favour of the gaseous $CO_2$ in the acid plasmatic water 30a in recirculation. The gaseous $CO_2$ is then removed through the action of the oxygenator 9. In this way, $CO_2$ removal from plasmatic water can be improved.

The $CO_2$-free acid plasmatic water 30a flowing out of the oxygenator 9 is brought back to the haemodiafilter 6, where it will work as a dialysis liquid. Therefore, the blood flowing out of the haemodiafilter 6 will have an electrolyte imbalance due to the exchange of electrolytes and gas with the $CO_2$-free acid plasmatic water 30a. Hence, in order to re-establish a balance in the concentration of electrolytes in the blood, before the latter is returned to the patient, downstream of the haemodiafilter 6 the basic plasmatic water 30b flowing out of the chamber 22 of the electrodialyzer 10 joins, through the line 11, the blood flowing out of the haemodiafilter 6 in the joining point 17. Along the line 11 there can be provided a filter 12 to hold back particles or particulate substances that might possibly be dangerous if reintroduced into the patient.

Finally, the blood is returned to the patient by means of a blood returning line 15.

Part of the basic plasmatic water 30b can also be recirculated along the line 13, where a precipitate removal unit 14 can be provided, for example a filter, a tangential filter or a centrifuge separator, which is designed to remove calcium precipitate, in order to then return to the inlet of the chamber 22 of the electrodialyzer 10.

Advantageously, the presence of the recirculation 13 of part of the basic plasmatic water 30b flowing out of the second chamber 22 of the electrodialyzer 10 upstream of the electrodialyzer 10 itself allows the plasmatic water to be basified in the circuit 7 upstream of the electrodialyzer and, as a consequence, triggers the precipitation of calcium and magnesium salts, mainly calcium carbonates, upstream of the device 14 used to remove said precipitate from the plasmatic water. Therefore, the liquid flowing out of the device is poor in calcium and magnesium and lacks precipitate. Hence, it can be sent to the electrodialyzer 10, where, even though subject to a further pH increase on the inside of the chamber 22, it will not cause a further precipitation of calcium and magnesium salts, thus keeping the efficiency of the electrodialyzer 10 high and avoiding the embolisation in the patient of precipitate of calcium and magnesium salts, which would occur in the absence of the recirculation 13 and the device 14.

In the circuit of FIG. 1, for example, the blood flow flowing out of the patient can be set at 200-500 ml/min, the flow of plasmatic water through the first chamber 21 can be set at 400-800 ml/min and the flow of the recirculation of the basic plasmatic water 30b can be set at 100-150 ml/min. The electrical current applied to the electrodialyzer 10 can range from 8 to 10 amperes. The gas flow on the inside of the oxygenator 9 can be 10 l/min.

Figure 3:
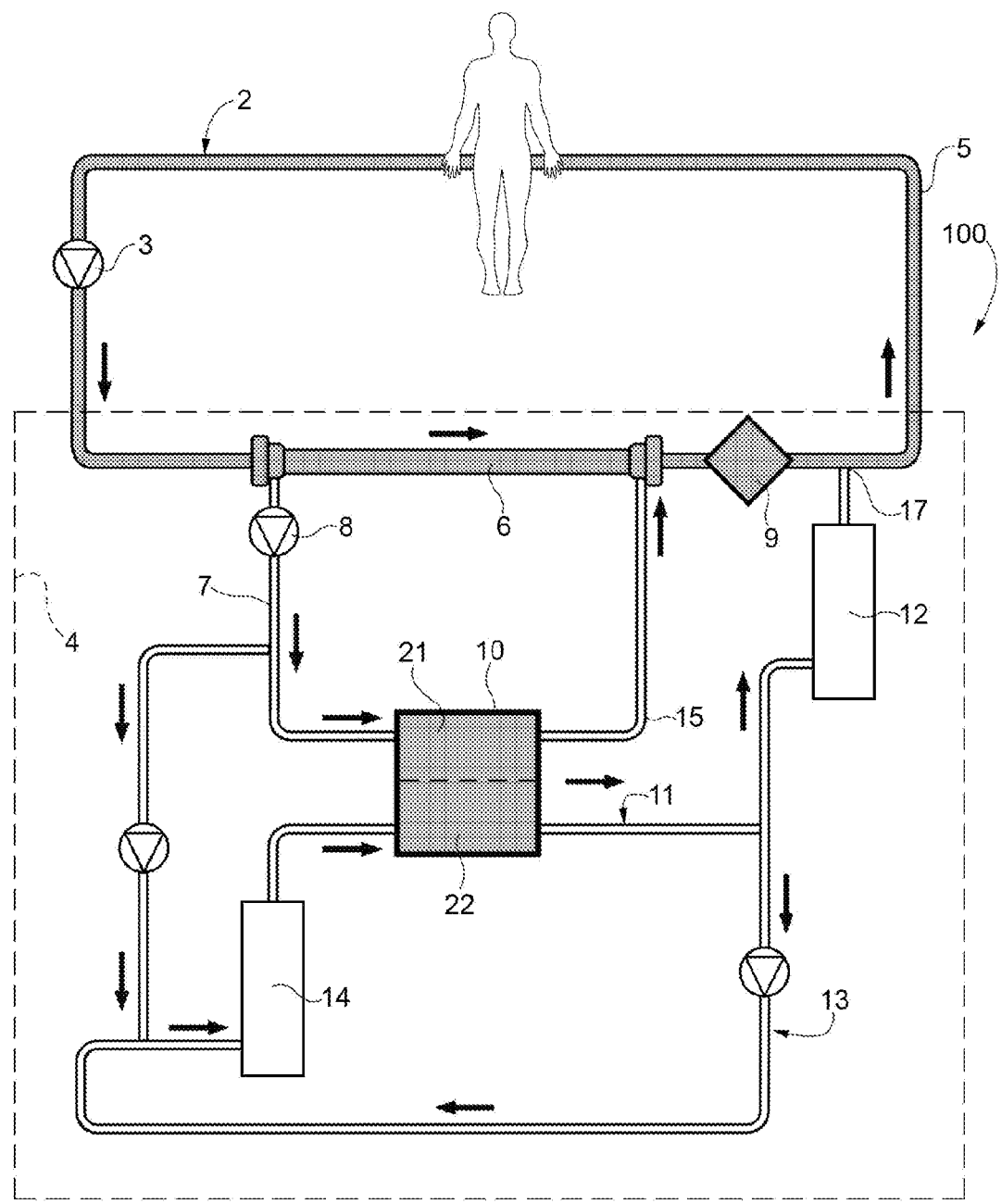
FIG. 3 shows a second embodiment of the invention.
Figure 4:
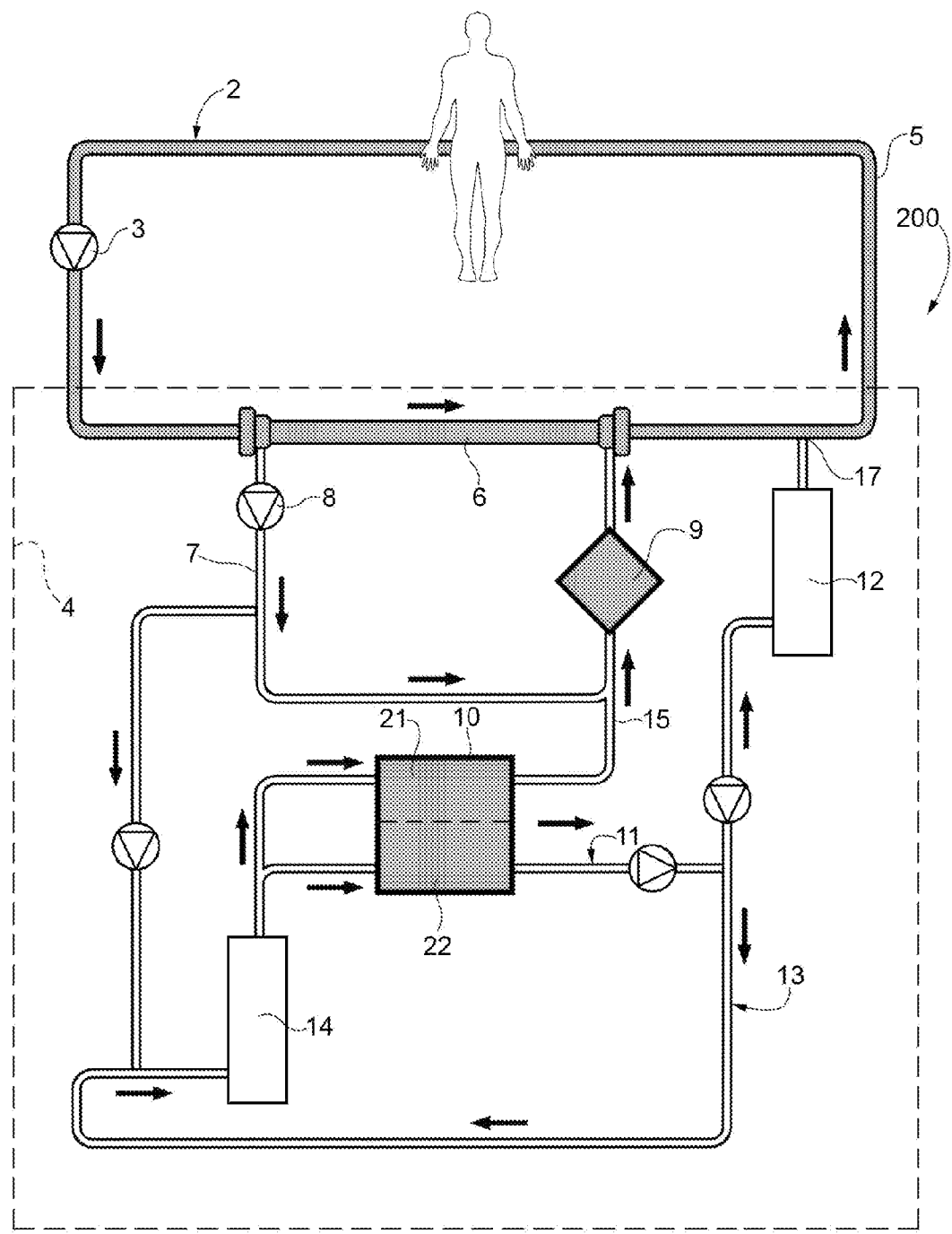
FIG. 4 shows a third embodiment of the invention.
Figure 5:
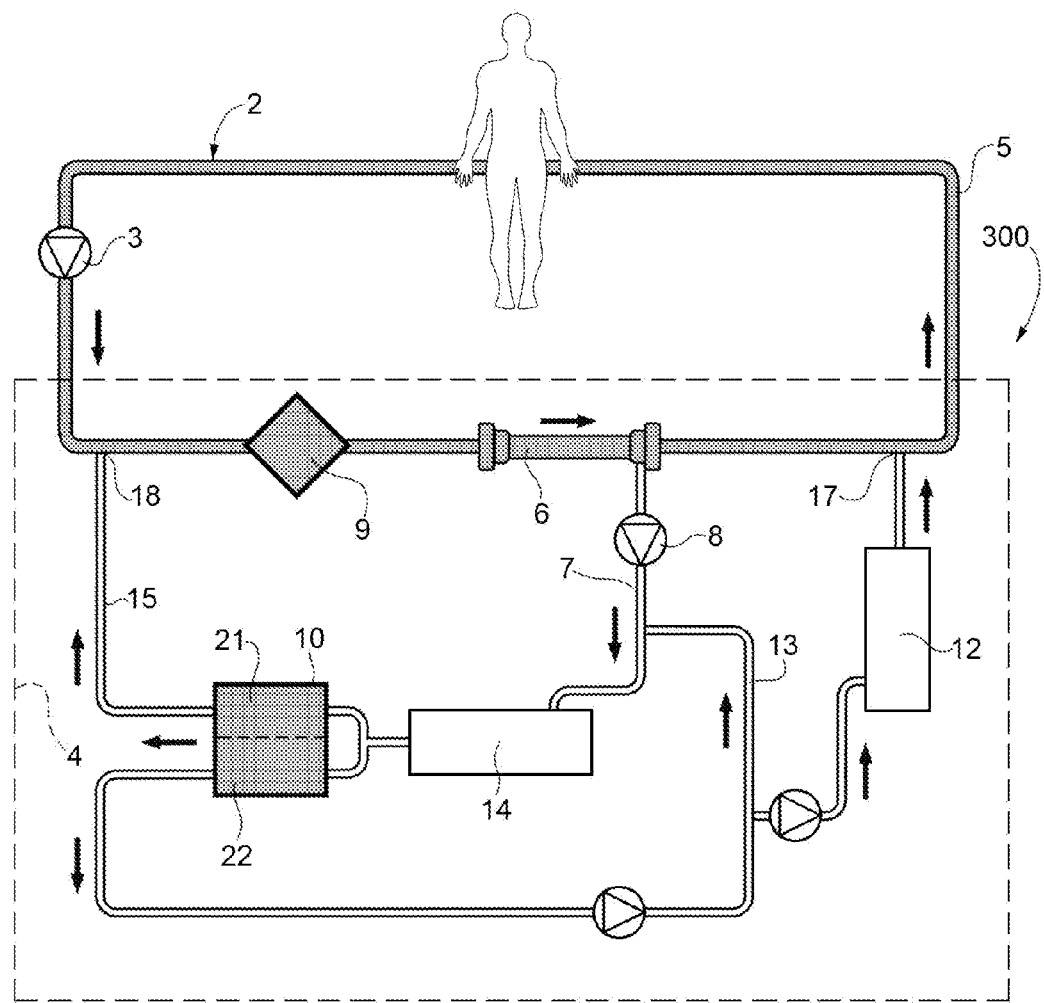
FIG. 5 shows a fourth embodiment of the invention.

FIGS. 3-5 show alternative embodiments of the circuit of FIG. 1 according to the present invention;

details that are similar or identical to the ones already described above are indicated, for the sake of simplicity, with the same reference numbers.

In particular, FIG. 3 shows a second embodiment of the present invention with a variant 100 of the circuit shown in FIGS. 1. In this case, the oxygenator 9 is arranged downstream of the haemodiafilter 6 on the line for returning blood 5 to the patient and upstream of the joining point 17 for the basic plasmatic water 30b. In this embodiment the oxygenator 9 is a membrane oxygenator. Furthermore, by way of example, in this embodiment the blood flow flowing out of the patient can be set at 200-500 ml/min, the flow of ultrafiltrate from the haemodiafilter can be set at 400-800 ml/min, the flow of plasmatic water through the second chamber 22 can be set at 100-150 ml/min, whereas the flow of the basic plasmatic water reintroduced into the line 5 for returning blood to the patient can be set at 30-50 ml/min. The electrical current applied to the electrodialyzer 10 can range from 8 to 10 amperes. The gas flow on the inside of the oxygenator 9 can be 5-10 l/min.

FIG. 4 shows a further variant 200 of the circuit of FIG. 1, wherein the electrodialyzer 10 is arranged on a circuit that is parallel to the ultrafiltrate circuit 7. In this case, part of the ultrafiltrate is directly led towards the oxygenator 9 and another part is led towards the electrodialyzer 10. The acid plasmatic water 30a is then reintroduced into the circuit 7 upstream of the oxygenator through the line 15. In this embodiment the oxygenator 9 can be a bubble oxygenator. In the embodiment of FIG. 4, for example, the blood flow flowing out of the patient can be set at 250 ml/min, the flow of plasmatic water through the oxygenator can be set at 400-800 ml/min, the flow of ultrafiltrate from the haemodiafilter, which is taken from the circuit 7 and heads for the chamber 21 of the electrodialyzer, can be set at 30-50 ml/min, whereas the flow of plasmatic water flowing through the second chamber 22 of the electrodialyzer 10 can be set at 50-200 ml/min. The electrical current applied to the electrodialyzer 10 can range from 8 to 10 amperes. The gas flow on the inside of the oxygenator 9 can be 10 l/min.

In FIG. 5, number 300 indicates a variant of the circuit according to the present invention.

The blood, taken from the patient through the line 2, is pushed by the peristaltic pump 3 towards the oxygenator 9 and subsequently towards the haemodiafilter 6. After having flown out of the haemodiafilter 6, the blood is returned to the patient through the line 5 for returning blood to the patient. In this embodiment the oxygenator is a membrane oxygenator.

The ultrafiltrate of the haemodiafilter 6 is led by the circuit 7 through a precipitate removal unit 14 designed to remove calcium and is then divided into two flows: a first flow enters the "acid" chamber 21 of the electrodialyzer 10 and a second flow enters the "basic" chamber 22 of the electrodialyzer 10. The acid plasmatic water 30a flowing out of the chamber 21 is recirculated in the blood taking line 2 upstream of the oxygenator in the direction of circulation of the blood in the joining point 18. The basic plasmatic water 30b flowing out of the chamber 22 of the electrodialyzer 10 is recirculated partly in the circuit 7 upstream of the precipitate removal unit 14 designed for the removal of calcium in the direction of circulation of the ultrafiltrate and partly in the line for returning blood 5 to the patient in the joining point 17.

In the embodiment of FIG. 5, for example, the blood flow flowing out of the patient can be set at 200-500 ml/min, whereas the flow of plasmatic water heading for the electrodialyzer can be set at 100-400 ml/min. The electrical current applied to the electrodialyzer 10 can range from 8 to 10 amperes. The oxygen flow on the inside of the oxygenator 9 can be 10 l/min.

The circuit shown in FIG. 3 was tested on healthy pigs, setting a blood flow (pump 3) of 250 ml/min. Extracorporeal $CO_2$ removal with the electrodialysis on and set at 10 amperes increased approximately by 100% compared to the values obtained with the electrodialysis off. The acid-basic and hydro-electrolyte systemic balance of the pig was not subject to alterations, only the systemic calcium, as to be expected in case of methods with electrodialysis, requested a reintegration obtained through intravenous infusion of a solution containing calcium. No hemolysis occurred and the system proved to be safe and effective.

Figure 6:
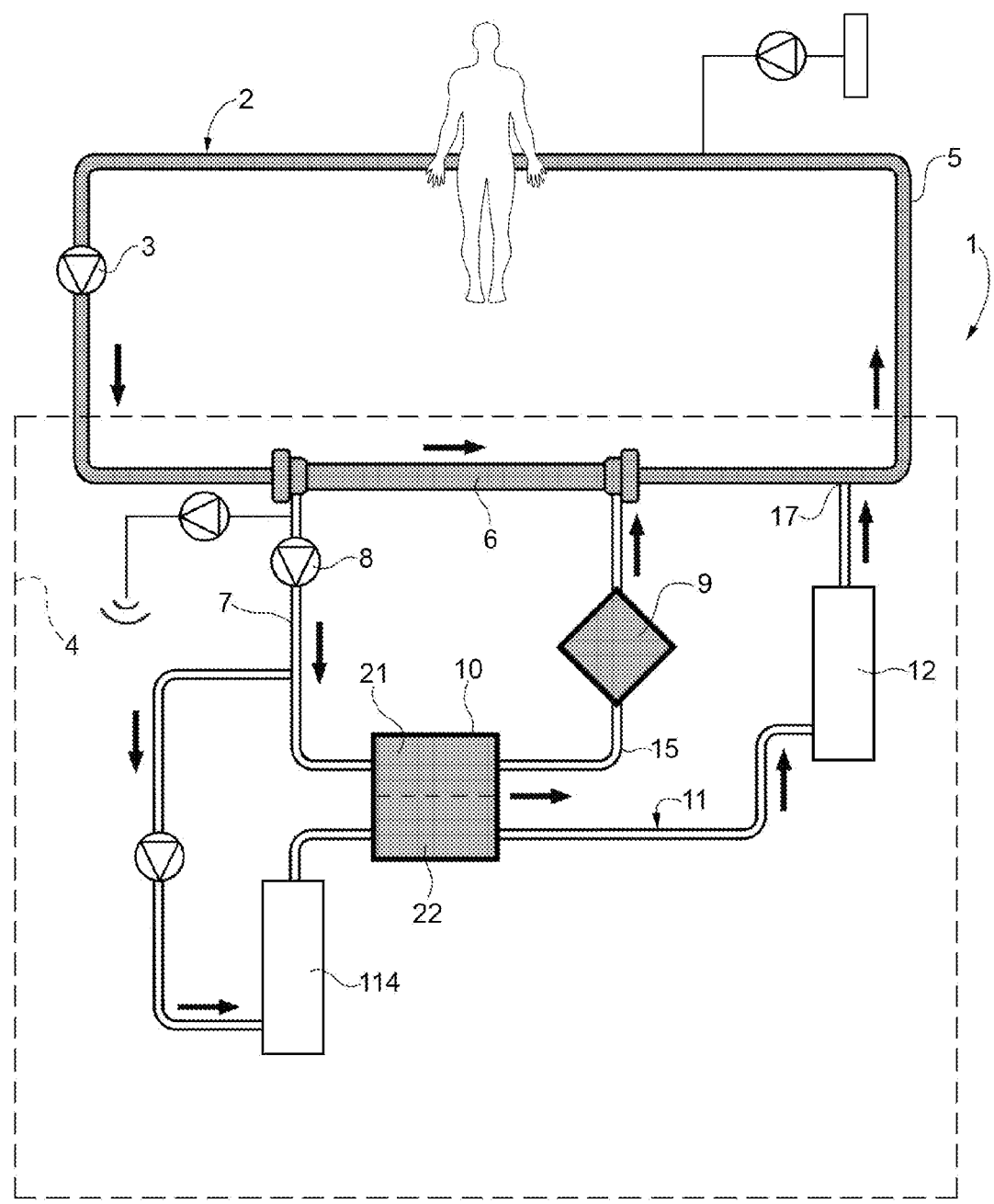
FIG. 6 shows a fifth embodiment of the invention.

Both in the embodiment of FIG. 1 and in the embodiments of FIGS. 3, 4 and 5, alternatively, the removal of calcium can be operated by replacing the precipitate removal unit 14 with a cartridge 114 containing a cationic ion-exchange resin, for example loaded with a solution containing 145 mEq/l of sodium and 4 mEq/l of potassium. As shown in FIG. 6, with reference to the embodiment of FIG. 1, in this case there is no need any longer to recirculate the solution 30b along the line 13, in order to basify the plasmatic water and help the precipitation of calcium. The system of this embodiment must be provided, upstream of the pump 8, with a system for removing part of the plasmatic water and, along the line for returning blood 5 to the patient, with a system for the infusion of a replacement liquid poor in sodium and rich in calcium, which are suited to the keep the hydro-electrolyte balance.

The invention claimed is:

1. An extracorporeal circuit for $CO_2$ removal from blood comprising:
   a line for taking blood from the patient;
   a decarboxylation assembly, comprising:
      a first filtering unit;
      an oxygenator;
      an electrodialyzer adapted to generate an acid solution and a basic solution; and
      a means for the infusion of said acid solution upstream of said oxygenator; and
   a line for returning the blood to the patient, wherein said electrodialyzer comprises a first electrodialysis chamber and a second electrodialysis chamber, said first and second electrodialysis chambers being separated by an ionic membrane, and wherein said first chamber and said second chamber are respectively separated from a positive electrode, or anode, and from a negative electrode, or cathode, by means of a bipolar membrane.

2. An extracorporeal circuit for $CO_2$ removal from blood according to claim 1, wherein said first filtering unit is a filter selected in the group consisting of a haemodiafilter, a haemofilter and a dialyzer.

3. An extracorporeal circuit for $CO_2$ removal from blood according to claim 1, further comprising a precipitate removal unit arranged upstream of the electrodialyzer.

4. An extracorporeal circuit for $CO_2$ removal from blood according to claim 3, wherein said precipitate removal unit is a system adapted for the removal of calcium precipitate.

5. An extracorporeal circuit for $CO_2$ removal from blood according to claim 4, wherein said precipitate removal unit is selected from the group consisting of a filter, a tangential filter and a centrifuge separator.

6. An extracorporeal circuit for $CO_2$ removal from blood according to claim 1, wherein said circuit comprises a plasmatic water circuit.

7. An extracorporeal circuit for $CO_2$ removal from blood according to claim 1, wherein said acid solution is acid plasmatic water.

8. An extracorporeal circuit for $CO_2$ removal from blood according to claim 1, further comprising an infusion means for the infusion of a basic solution downstream of said first filtering unit on the line for returning the blood to the patient.

9. An extracorporeal circuit for $CO_2$ removal from blood according to claim 1, further comprising a means for the recirculation of a basic solution upstream of the electrodialyzer.

10. An extracorporeal circuit for $CO_2$ removal from blood according to claim 3, wherein a basic solution is recirculated upstream of said precipitate removal unit.

11. An extracorporeal circuit for $CO_2$ removal from blood according to claim 1, wherein said decarboxylation assembly further comprises a cartridge containing a cationic ion-exchange resin arranged upstream of the electrodialyzer.

12. An extracorporeal circuit for $CO_2$ removal from blood according to claim 1, wherein the positive electrode and the negative electrode are respectively arranged in a chamber containing an anolyte solution and in a chamber containing a catholyte solution, said anolyte solution and catholyte solution respectively recirculating to the chambers along lines where degassers are present.

* * * * *